US012653775B2

(12) United States Patent
Mannala et al.

(10) Patent No.: US 12,653,775 B2
(45) Date of Patent: Jun. 16, 2026

(54) CANINE TOPICAL FORMULATIONS AND METHODS THEREOF

(71) Applicants: Shajan Mannala, Oldsmar, FL (US); Samantha Mannala, Oldsmar, FL (US); Sonya Mannala, Oldsmar, FL (US)

(72) Inventors: Shajan Mannala, Oldsmar, FL (US); Samantha Mannala, Oldsmar, FL (US); Sonya Mannala, Oldsmar, FL (US)

( * ) Notice: Subject to any disclaimer, the term of this patent is extended or adjusted under 35 U.S.C. 154(b) by 462 days.

(21) Appl. No.: 18/160,753

(22) Filed: Jan. 27, 2023

(65) Prior Publication Data

US 2024/0252427 A1     Aug. 1, 2024

(51) Int. Cl.
| | |
|---|---|
| *A61K 9/00* | (2006.01) |
| *A61K 31/155* | (2006.01) |
| *A61K 31/164* | (2006.01) |
| *A61K 31/4174* | (2006.01) |
| *A61K 33/38* | (2006.01) |
| *A61K 47/20* | (2006.01) |
| *A61P 17/02* | (2006.01) |
| *A61P 17/04* | (2006.01) |
| *A61P 31/04* | (2006.01) |

(52) U.S. Cl.
CPC .......... *A61K 9/0017* (2013.01); *A61K 31/155* (2013.01); *A61K 31/164* (2013.01); *A61K 31/4174* (2013.01); *A61K 33/38* (2013.01); *A61K 47/20* (2013.01); *A61P 17/02* (2018.01); *A61P 17/04* (2018.01); *A61P 31/04* (2018.01)

(58) Field of Classification Search
CPC .. A61K 9/0017; A61K 31/155; A61K 31/164; A61K 31/4174; A61K 33/38; A61K 47/20; A61K 9/10; A61K 47/18; A61P 17/02; A61P 17/04; A61P 31/04
See application file for complete search history.

(56) References Cited

U.S. PATENT DOCUMENTS

| | | | | |
|---|---|---|---|---|
| 5,650,145 A * | 7/1997 | Saint-Leger | ......... | A61K 31/155 424/DIG. 5 |
| 6,294,186 B1 * | 9/2001 | Beerse | .................... | A61P 31/12 514/156 |
| 2004/0142020 A1 * | 7/2004 | Jones | .................. | A61L 26/0052 424/445 |
| 2004/0219122 A1 * | 11/2004 | Masuda | ................. | A61K 8/345 424/70.12 |
| 2007/0081958 A1 * | 4/2007 | Bechert | .................. | A61P 31/02 424/618 |
| 2012/0058167 A1 * | 3/2012 | Widgerow | ........... | A61K 9/1647 424/769 |
| 2012/0201902 A1 * | 8/2012 | Modak | ...................... | A61P 9/06 424/618 |
| 2013/0204213 A1 * | 8/2013 | Heagle | .................... | A61M 1/98 604/385.01 |
| 2016/0045635 A1 * | 2/2016 | Jayakody | ................ | A61P 31/02 264/45.3 |
| 2018/0250208 A1 * | 9/2018 | Boice | ..................... | A61K 8/498 |
| 2021/0353814 A1 * | 11/2021 | Fields | ................... | A61Q 15/00 |
| 2022/0112322 A1 * | 4/2022 | Liu | ....................... | C08F 230/08 |

OTHER PUBLICATIONS

S. Finnegan et al., "EDTA: An Antimicrobial and Antibiofilm Agent for Use in Wound Care," Advances in Wound Care, vol. 4, No. 7, published Jun. 5, 2015, p. 415-421.*
K. A. Moriello, "In vitro efficacy of shampoos containing miconazole, ketoconazole, climbazole or accelerated hydrogen peroxide against Microsporum canis and Trichophyton species," Journal of Feline Medicine and Surgery 2017, vol. 19(4) 370-374.*
Debabov D, Noorbaksh C, Mannala S, Steinrucke P, Moreau P and Rosenkrantz W, In vitro activity of micronized silver and a micronized silver-containing shampoo against *Staphylococcous intermedius* and *Pseudomonas aeruginosa*, 2016, The Authors, Veterinary Dermatology, 27 (Suppl. 1), 6-21.
Borio S, Colombo S, La Rosa G, De Lucia M, Damborg P and Guardabass L, Effectiveness of a combined (4% chlorhexidine gluconate shampoo and solution) protocol in MRS and non-MRS canine superficial pyoderma; a randomized, blinded, antibiotic-controlled study, Veterinary Dermatology, 2015, 26: 339-e72; doi: 10.1111/vde.12233.
Loeffler A, Cain CL, Ferrer L, Nishifuji K, Varjonen K, Papich MG, Guardabassil, Frosini SM, Barker EN and Weese JS, Antimicrobial use guidelines for canine pyoderma by the International Society for Companion Anima Infectious Diseases (ISCAID), Veterinary Dermatology, 2025, 36:234-282, doi: 10.1111/vde.13342.
Bajwa J, Canine superficial pyoderma and therapeutic considerations, CVJ, 2016, 57:204-206.
Sykes JE, Nagle TM and White SD, Chapter 84—Pyoderma, Otitis Externa and Otitis Media, Cznine and Feline Infectious Diseases, 2014, pp. 800-813, https://doi.org/10.1016/B978-1-4377-0795-3.00084-3, (https://www.sciencedirect.com/science/article/pii/B9781437707953000843).
Taylor C, Shampooing dogs: facts and myths, 2011, https://www.veterinary-practice.com/article/shampooing-dogs-facts-and-myths.

* cited by examiner

*Primary Examiner* — Monica A Shin
(74) *Attorney, Agent, or Firm* — Jyoti C. Iyer

(57) ABSTRACT

A canine topical formulation having chlorhexidine gluconate and a silver component. A canine topical formulation having chlorhexidine gluconate, a silver component, an azole component and/or a salt of an azole component and a ceramide. Methods of treating canine secondary superficial bacterial pyoderma by administering canine topical formulations. Methods of improving skin conditioning in canines. Methods of treating secondary superficial bacterial pyoderma in a dog by administering a shampoo formulation.

32 Claims, 1 Drawing Sheet

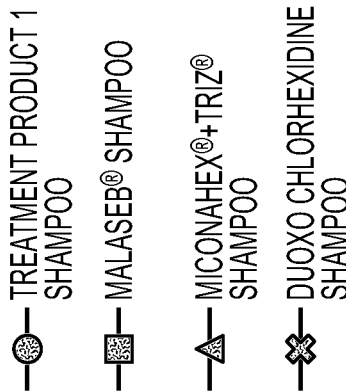
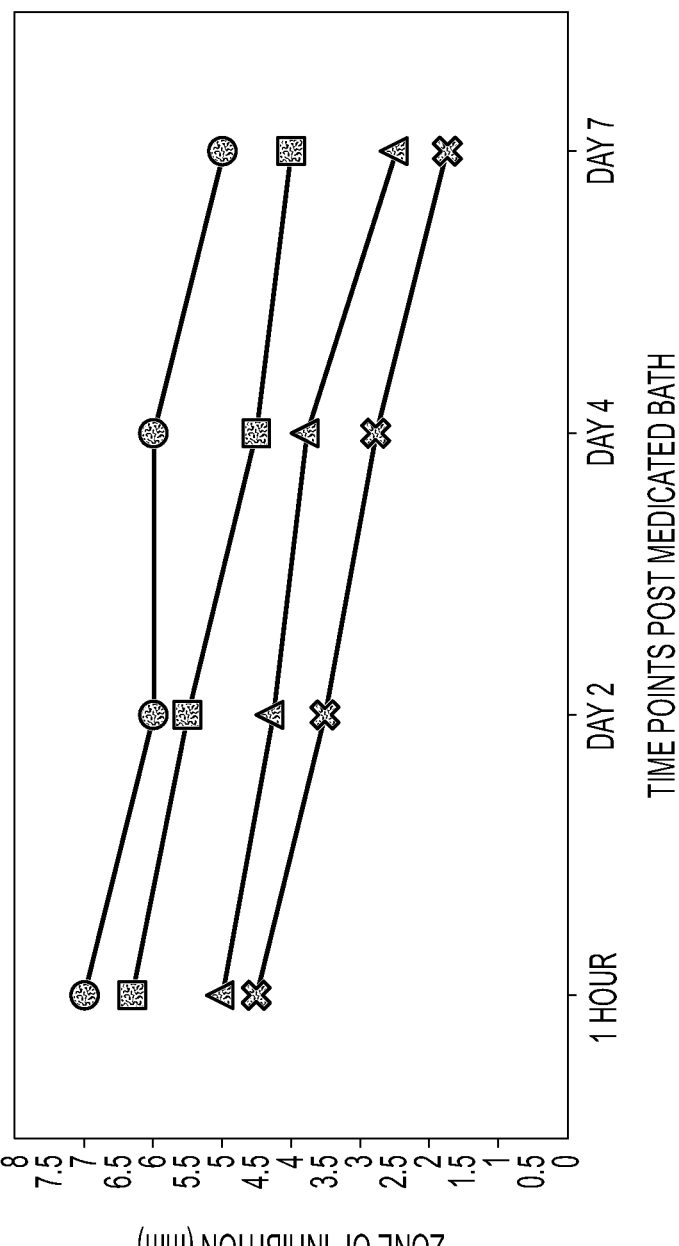

CANINE TOPICAL FORMULATIONS AND METHODS THEREOF

FIELD

This disclosure relates to canine topical formulations and methods for treating canine superficial bacterial pyoderma.

BACKGROUND OF THE INVENTION

In this section, we discuss several aspects of related work, including background and conventional technologies.

Canine secondary superficial bacterial pyoderma (SSBP) is a bacterial infection confined to the superficial portion of the skin. Bacteria may cause an infection secondary to local trauma, scratching, contamination due to poor grooming, seborrhea, parasitic infestation, hormonal factors, local irritants, or allergies. In dogs, SSBP is the most common form of pyoderma, and is also the principal reason for antimicrobial use in small animal practice. The predominant pathogen that causes superficial pyoderma is *Staphylococcus pseudintermedius*, a commensal bacterium that resides on the mucosal and skin surfaces of dogs and other canines.

Superficial bacterial pyoderma can often become a chronic and/or recurrent condition if the primary underlying cause is not identified and adequately resolved or controlled. Causes for the persistence or recurrence of pyoderma include inappropriate therapy (drugs used, duration of treatment), lack of diagnostics, methicillin resistance, client compliance. These and other factors such as bacterial carriage on individual dogs, immune suppression, and persistent underlying disease can lead to selection of methicillin-resistant staphylococci in a patient.

Since 2006, methicillin-resistant *S. pseudintermedius* (MRSP) has emerged as a significant problem in veterinary medicine, due to its clonal spread in Europe and North America. Resistance is mediated by the mecA gene, which encodes the modified penicillin-binding protein (PBP) that prevents antibiotics from binding and disrupting cell wall construction, allowing the bacterium to survive and proliferate.

*Staphylococcus pseudintermedius* is primarily identified in dogs and is rare in other species, although it has been identified in other species, including cats, horses, and humans. While *S. pseudintermedius* is regarded as a canine-specific pathogen that is restricted to skin infection, there are reports of postoperative infections in dogs, and infections in humans.

Biofilms are densely packed communities of bacterial cells that grow on the surface of organic or inorganic substances. The icaoperon is known to encode polysaccharide intercellular adhesion molecules that facilitate adhesion between proliferating cells, which is essential for bacterial cell accumulation. Several studies reported that MRSP, also has an ability to produce biofilms. However, biofilm-related problems have not been evaluated and fully addressed in topical treatment protocols.

Antibiotic resistance is one of the important problems encountered in treatment and control of *S. pseudintermedius* infection. Pyoderma caused by resistant bacteria is difficult to cure and has severe consequences.

Biofilm formation has increasingly been accepted as an important virulence factor and it is important for bacterial persistence and survival in the environment. The low susceptibility to antibiotics appears to be attributed to insufficient penetration of antibiotics into biofilm (which in turn will lead antibiotic resistance because of sublethal MICs), to the reduced growth rate of bacteria embedded in biofilm, and to the wide variety of altered metabolic states within the biofilms that are necessary for cell survival in hostile environments. Within a biofilm, bacteria are able to evade the host immune response and antimicrobials effects through physical and chemical protection of the biofilm matrix.

SUMMARY OF THE INVENTION

Disclosure provides a canine topical formulation having chlorhexidine gluconate and a silver component.

Disclosure provides a canine topical formulation wherein the chlorhexidine ranges from about 2% to about 4% by weight of the canine topical formulation. In some embodiments, the chlorhexidine gluconate is about 2% by weight of the canine topical formulation.

Disclosure provides a canine topical formulation having a silver component. The silver component is selected from the group consisting of an elemental silver, micronized silver, nano silver, a colloidal silver, a silver salt, or combinations thereof. The silver salt is selected from the group consisting of silver nitrate, silver chloride, silver sulfadiazine, or combinations thereof. The silver component ranges from about 0.08% to about 0.12% by weight of the canine topical formulation. Disclosure provides canine topical formulations wherein the silver component is about 0.1% by weight of the canine topical formulation. In some canine topical formulations, the silver component is elemental silver. In some canine topical formulations, the elemental silver ranges from about 0.08% to about 0.12% by weight of the canine topical formulation. In some canine topical formulations, the elemental silver is about 0.1% by weight of the canine topical formulation.

Disclosure provides canine topical formulations, wherein the chlorhexidine gluconate ranges from about 2% to about 4% by weight of the canine topical formulation, and wherein the silver component ranges from about 0.08% to about 0.12% by weight of the canine topical formulation. Disclosure provides canine topical formulations, wherein the chlorhexidine gluconate is about 2% by weight of the canine topical formulation, and wherein the silver component is about 0.1% by weight of the canine topical formulation. Disclosure provides canine topical formulations, wherein the chlorhexidine gluconate is about 2% by weight of the canine topical formulation, and wherein the silver component is elemental silver, and wherein the elemental silver is about 0.1% by weight of the canine topical formulation.

Disclosure provides canine topical formulations having an azole component. The azole component is selected from the group consisting of ketoconazole, miconazole, fluconazole, itraconazole, econazole, climbazole or combinations thereof. The azole component ranges from about 0.25% to about 2.2% by weight of the canine topical formulation.

Disclosure provides canine topical formulations having a salt form of an azole component, wherein the azole component is selected from the group consisting of ketoconazole, miconazole, fluconazole, itraconazole, econazole, climbazole or combinations thereof, and wherein the salt form is selected from the group consisting of a chloride, a nitrate, an amine, or combinations thereof. The salt of the azole component ranges from about 0.25% to about 2.2% by weight of the canine topical formulation. Disclosure provides canine topical formulations having miconazole nitrate as the salt of the azole component. The miconazole nitrate ranges from about 1.8% to about 2.2% by weight of the canine topical formulation. In some embodiments, the miconazole nitrate is about 2% by weight of the canine topical formulation.

Disclosure provides canine topical formulations:

wherein the chlorhexidine gluconate ranges from about 2% to about 4% by weight of the canine topical formulation;

wherein a silver component ranges from about 0.08% to about 0.12% of the canine topical formulation; and wherein miconazole nitrate ranges from about 1.8% to about 2.2% by weight of the canine topical formulation.

Disclosure provides canine topical formulations, wherein chlorhexidine gluconate is about 2% by weight of the canine topical formulation;

wherein the silver component is about 0.1% by weight of the canine topical formulation; and wherein the miconazole nitrate is about 2% by weight of the canine topical formulation.

Disclosure provides canine topical formulations, wherein chlorhexidine gluconate ranges from about 2% to about 4% by weight of the canine topical formulation;

wherein a silver component ranges from about 0.08% to about 0.12% of the canine topical formulation; and wherein the azole component ranges from about 0.25% to about 2.2% by weight of the canine topical formulation.

Disclosure provides canine topical formulations, wherein the chlorhexidine gluconate ranges from about 2% to about 4% by weight of the canine topical formulation;

wherein the silver component ranges from about 0.08% to about 0.12% of the canine topical formulation; and wherein the salt of the azole component ranges from about 0.25% to about 2.2% by weight of the canine topical formulation.

Disclosure provides canine topical formulations having a ceramide selected from the group consisting of ceramide 1 (or ceramide EOP), ceramide 2 (or ceramide NS or NG), ceramide 6-II (ceramide NP), ceramide 9 (or ceramide EOP), phytosphingosine, sphingosine, ceramide 3 (or N-Octadecanoylphytosphingosine), or combinations thereof. The ceramide ranges from about 0.02% to about 0.05% by weight of the canine topical formulation. Disclosure provides canine topical formulations, wherein the ceramide is ceramide 3 (or N-Octadecanoylphytosphingosine). The ceramide 3 (or N-Octadecanoylphytosphingosine) ranges from about 0.025% to about 0.05% by weight of the canine topical formulation. In some embodiments, the ceramide 3 (or N-Octadecanoylphytosphingosine) is about 0.05% by weight of the canine topical formulation.

Disclosure provides canine topical formulations, wherein the chlorhexidine gluconate ranges from about 2% to about 4% by weight of the canine topical formulation;

the azole component ranges from about 0.25% to about 2.2% by weight of the canine topical formulation;

the silver component ranges from about 0.8% to about 0.12% by weight of the canine topical formulation; and the ceramide ranges from about 0.02% to about 0.05% by weight of the canine topical formulation.

Disclosure provides canine topical formulations, wherein the chlorhexidine gluconate is about 2% by weight of the canine topical formulation;

the miconazole nitrate is 2% by weight of the canine topical formulation;

the elemental silver is about 0.1% by weight of the canine topical formulation; and the ceramide 3 (or N-Octadecanoylphytosphingosine) is about 0.05% by weight of the canine topical formulation.

Disclosure provides canine topical formulations having tris ethylene diamine tetra acetic acid (EDTA).

Disclosure provides canine topical formulations having:

a component selected from the group consisting of a solvent, an extender, an emulsifier, a surfactant, a suspending agent, a foam booster, a fragrance, and combinations thereof.

Disclosure provides canine topical formulations having purified water, sodium laureth sulfate, sodium lauryl sulfate, cocamidopropyl betaine, acrylates copolymer, Polysorbate 20, ethylene glycol monostearate, triethanolamine, kiwi fragrance, titanium dioxide (and) synthetic fluorphlogopite, methylchloroisothiazolinone and methylisothiazolinone.

The canine topical formulation can be a shampoo, a conditioner, a leave-on product, an ointment, a cream, a spray, or combinations thereof. Disclosure provides some embodiments of canine topical formulations, wherein the canine topical formulation is a shampoo.

Disclosure provides in some embodiments a canine topical formulation for treating a canine in need thereof. The canine can be a dog, a cat or a horse. In some embodiments, the disclosure provides a canine topical formulation for treating a dog. In some embodiments, the canine topical formulation for treating a dog is shampoo.

Some embodiments provide methods for treating and decreasing reinfection of canine secondary superficial bacterial pyoderma comprising treating a canine in need thereof with canine topical formulations.

Some embodiments provide methods of decreasing a biofilm of *S. pseudintermedius* by treating a canine in need thereof with canine topical formulations.

Some embodiments provide methods of decreasing a biofilm of a clinical isolate of *S. pseudintermedius* by treating a canine in need thereof with canine topical formulation.

Disclosure provides methods of decreasing a biofilm of *Pseudomonas aeruginosa* by treating a canine in need thereof with a canine topical formulation.

Disclosure provides methods of decreasing a biofilm of a clinical isolate of *Pseudomonas aeruginosa* by treating a canine in need thereof with a canine topical formulation.

Disclosure provides methods of decreasing a biofilm of MSRP clinical isolate of *Pseudomonas aeruginosa* by treating a canine in need thereof with a canine topical formulation.

Disclosure provides methods of decreasing a biofilm of multidrug resistant (MDR) clinical isolate of *Pseudomonas aeruginosa* by treating a canine in need thereof with a canine topical formulation.

Disclosure provides methods of decreasing treatment duration of canine secondary superficial bacterial pyoderma by treating a canine in need thereof with a canine topical formulation.

Disclosure provides methods of decreasing frequency of canine secondary superficial bacterial pyoderma by treating a canine in need thereof with a canine topical formulation.

Disclosure provides methods of increasing treatment compliance during treatment of canine secondary superficial bacterial pyoderma by treating a canine in need thereof with a canine topical formulation.

Disclosure provides methods of improving a skin condition of a canine affected with secondary superficial bacterial pyoderma due to the residual activity of pathogens by treating the canine in need thereof with a canine topical formulation. The skin conditions treated can be seborrhea, erythema, lesional spreading and pruritus.

Disclosure provides methods of improving skin conditioning in a canine having canine secondary superficial bacterial pyoderma (SSBP) by treating the canine in need thereof with a canine topical formulation.

Disclosure provides methods of treating canine secondary superficial bacterial pyoderma by applying a canine topical formulation topically once a week for two weeks.

Disclosure provides methods of treating canine secondary superficial bacterial pyoderma by treating a canine in need thereof with the canine topical formulation whereby reinfection is decreased.

Disclosure provides methods of preparing a canine topical formulation, wherein the canine topical formulation includes chlorhexidine gluconate, an azole component, a silver component and a ceramide, wherein the method of preparing the canine topical formulation includes:

preparing a mixture having chlorhexidine gluconate, the azole component and a surfactant to form a first mixture;

mixing the ceramide with the first mixture to form a second mixture;

adding a suspension-premix of the silver component into the second mixture to obtain a third mixture;

stirring the third mixture at a temperature below 40 degrees Celsius until a stirred third mixture is obtained, wherein the stirred third mixture is the canine topical formulation, wherein the surfactant is selected from the group consisting of sodium lauryl sulfate and sodium laureth sulfate, wherein the suspension-premix of the silver component is prepared by suspending the silver component in a suspending agent, and wherein the suspending agent is selected from the group consisting of cocamidopropyl betaine, acrylates copolymer, polysorbate 20, ethylene glycol monostearate, triethanolamine and combinations thereof.

BRIEF DESCRIPTION OF THE DRAWINGS

The above objectives and advantages of the disclosed teachings will become more apparent by describing in detail preferred embodiments thereof with reference to the attached drawings in which:

FIG. 1 Residual In Vitro Activity of Canine Hair Against *Staphylococcus pseudintermedius*. Circles (Treatment Product 1); Squares (Malaseb® Shampoo); triangles (Miconahex®+Trix® Shampoo); cross or x (DUOXO® Chlorhexidine Shampoo).

DETAILED DESCRIPTION OF THE INVENTION

The disclosure provides formulations and methods for treating canine secondary superficial bacterial pyoderma and the progression/resolution of the respective clinical scores of seborrhea, erythema, lesional spreading and pruritus during the treatment period.

Inventors investigated the differences in the prevalence of antibiotic resistance by agar diffusion test. Results showed that *S. pseudintermedius* isolates had high antibiotic resistance. The high antimicrobial resistance rate in combination with biofilm production could explain the difficulty of treating *S. pseudintermedius* canine infections, chemotherapeutic failure and, consequently, the rapid emergence of this bacterium in veterinary hospitals worldwide. All these elements lead inventors to consider biofilm formation as a relevant marker of microbial virulence as well as an indicator of potentially dangerous strains, generally less sensitive to antibiotic treatment. Furthermore, there is evidence of MRSP transmission to humans, suggesting a possible zoonotic potential.

Inventors surprisingly found that ceramide III which is known to decrease transepidermal water loss thus improves skin moistures, acted synergistically with elemental silver (which is a skin conditioning agent) to improve skin condition and repair post-inflammatory, post-infection skin in canines having canine secondary superficial bacterial pyoderma.

In one aspect, the disclosure provides a canine topical formulation.

In some embodiments, the disclosure provides a canine topical formulation having chlorhexidine gluconate and a silver component.

In some embodiments of the canine topical formulation, the chlorhexidine ranges from about 2% to about 4% by weight of the canine topical formulation is provided. In some embodiments, the chlorhexidine gluconate is about 2% by weight of the canine topical formulation.

In some embodiments, a canine topical formulation having a silver component is provided. The silver component can be an elemental silver, micronized silver, nano silver, a colloidal silver, a silver salt, or combinations thereof. The silver salt can be silver nitrate, silver chloride, silver sulfadiazine, or combinations thereof. The silver component ranges from about 0.08% to about 0.12% by weight of the canine topical formulation. Disclosure provides canine topical formulations wherein the silver component is about 0.1% by weight of the canine topical formulation. In some canine topical formulations, the silver component is elemental silver. In some canine topical formulations, the elemental silver can range from about 0.08% to about 0.12% by weight of the canine topical formulation. In some canine topical formulations, the elemental silver is about 0.1% by weight of the canine topical formulation.

In some embodiments of the canine topical formulations, the chlorhexidine gluconate ranges from about 2% to about 4% by weight of the canine topical formulation, and the silver component ranges from about 0.08% to about 0.12% by weight of the canine topical formulation. In some embodiments of the canine topical formulations, the chlorhexidine gluconate is about 2% by weight of the canine topical formulation, and the silver component is about 0.1% by weight of the canine topical formulation. Disclosure provides some embodiments of canine topical formulations, wherein the chlorhexidine gluconate is about 2% by weight of the canine topical formulation, and wherein the silver component is elemental silver, and wherein the elemental silver is about 0.1% by weight of the canine topical formulation.

Disclosure provides some embodiments of canine topical formulations having an azole component. The azole component can be ketoconazole, miconazole, fluconazole, itraconazole, econazole, climbazole or combinations thereof. The azole component can range from about 0.25% to about 2.2% by weight of the canine topical formulation.

Disclosure provides some embodiments of canine topical formulations having a salt form of an azole component, wherein the azole component can be ketoconazole, miconazole, fluconazole, itraconazole, econazole, climbazole or combinations thereof, and wherein the salt form of the azole component can be chloride, a nitrate, an amine, or combinations thereof. The salt of the azole component ranges from about 0.25% to about 2.2% by weight of the canine topical formulation. In some embodiments, the azole component ranges from about 1.8% to about 2.2% by weight of the canine topical formulation. Some embodiments provide canine topical formulations having miconazole as the azole component. In some embodiments, miconazole ranges from about 1.8% to about 2.2% by weight of the canine topical formulation. In some embodiments, miconazole is about 2% by weight of the canine topical formulation. In some embodiments, the salt of the azole component ranges from about 1.8% to about 2.2% by weight of the canine topical formulation. Some embodiments provide canine topical formulations having miconazole nitrate as the salt of the azole component. In some embodiments, the miconazole nitrate ranges from about 1.8% to about 2.2% by weight of the canine topical formulation. In some embodiments, the miconazole nitrate is about 2% by weight of the canine topical formulation.

Some embodiments of canine topical formulations have:
chlorhexidine gluconate ranging from about 2% to about 4% by weight of the canine topical formulation;
a silver component ranging from about 0.08% to about 0.12% of the canine topical formulation; and
miconazole nitrate ranging from about 1.8% to about 2.2% by weight of the canine topical formulation.
Disclosure provides some embodiments of canine topical formulations, wherein
chlorhexidine gluconate is about 2% by weight of the canine topical formulation;
wherein the silver component is about 0.1% by weight of the canine topical formulation; and
wherein the miconazole nitrate is about 2% by weight of the canine topical formulation.
Disclosure provides some embodiments of canine topical formulations, wherein chlorhexidine gluconate ranges from about 2% to about 4% by weight of the canine topical formulation;
wherein a silver component ranges from about 0.08% to about 0.12% of the canine topical formulation; and
wherein the azole component ranges from about 0.25% to about 2.2% by weight of the canine topical formulation.
Disclosure provides some embodiments of canine topical formulations,
wherein the chlorhexidine gluconate ranges from about 2% to about 4% by weight of the canine topical formulation;
wherein the silver component ranges from about 0.08% to about 0.12% of the canine topical formulation; and
wherein the salt of the azole component ranges from about 0.25% to about 2.2% by weight of the canine topical formulation.
Disclosure provides some embodiments of canine topical formulations having a ceramide selected from the group consisting of ceramide 1 (or ceramide EOP), ceramide 2 (or ceramide NS or NG), ceramide 6-II (ceramide NP), ceramide 9 (or ceramide EOP), phytosphingosine, sphingosine, ceramide 3 (or N-Octadecanoylphytosphingosine), or combinations thereof. The ceramide ranges from about 0.02% to about 0.05% by weight of the canine topical formulation. Disclosure provides canine topical formulations, wherein the ceramide is ceramide 3 (or N-Octadecanoylphytosphingosine). The ceramide 3 (or N-Octadecanoylphytosphingosine) ranges from about 0.025% to about 0.05% by weight of the canine topical formulation. In some embodiments, the ceramide 3 (or N-Octadecanoylphytosphingosine) is about 0.05% by weight of the canine topical formulation.

Disclosure provides some embodiments of canine topical formulations, wherein
the chlorhexidine gluconate ranges from about 2% to about 4% by weight of the canine topical formulation;
the azole component ranges from about 0.25% to about 2.2% by weight of the canine topical formulation;
the silver component ranges from about 0.8% to about 0.12% by weight of the canine topical formulation; and
the ceramide ranges from about 0.02% to about 0.05% by weight of the canine topical formulation.
Disclosure provides some embodiments of canine topical formulations, wherein
the chlorhexidine gluconate is about 2% by weight of the canine topical formulation;
the miconazole nitrate is 2% by weight of the canine topical formulation;
the elemental silver is about 0.1% by weight of the canine topical formulation; and
the ceramide 3 (or N-Octadecanoylphytosphingosine) is about 0.05% by weight of the canine topical formulation.
Disclosure provides some embodiments of canine topical formulations having tris ethylene diamine tetra acetic acid (EDTA).
Disclosure provides some embodiments of canine topical formulations having:
a component selected from the group consisting of a solvent, an extender, an emulsifier, a surfactant, a suspending agent, a foam booster, a fragrance, or combinations thereof. Examples of solvent is water. Examples of an extender is water. Example of emulsifiers are cocamidopropyl betaine and polysorbate 20. Examples of surfactants are sodium lauryl sulphate (SLS) and sodium laureth sulphate (SLES). Example of foam booster is cocamidopropyl betaine. Example of suspending agents are cocamidopropyl betaine, acrylates copolymer, polysorbate 20, ethylene glycol monostearate, triethanolamine and combinations thereof.
Sodium laureth sulfate (SLES or sodium lauryl ether sulfate), also called sodium alkylethersulfate, is an anionic detergent and surfactant.
Cocamidopropyl betaine is used as a foam booster in shampoos, emulsifying agent, thickener, antistatic agent.
Acrylates copolymer is a film-forming agent that is used in cosmetic and skin care products. It forms a barrier on the skin and results in a very soft and smooth.
Polysorbate 20 (Tween 20) is a surfactant and emulsifier.
Ceramide 3 consists of a phytosphingosine backbone N-acylated with a saturated fatty acid (stearic acid). It is widely used as a moisturizer in various cosmetic and personal products. Together with ceramide 1, they synergistically improve the skin barrier function.
Disclosure provides canine topical formulations having purified water, sodium laureth sulfate, sodium lauryl sulfate, cocamidopropyl betaine, acrylates copolymer, Polysorbate 20, ethylene glycol monostearate, triethanolamine, kiwi fragrance, titanium dioxide (and) synthetic fluorphlogopite, methylchloroisothiazolinone and methylisothiazolinone.
The canine topical formulation can be a shampoo, a conditioner, a leave-on product, an ointment, a cream, a spray, or combinations thereof. Disclosure provides a canine topical formulation, wherein the canine topical formulation is a shampoo.
Shampoo is a hair/skin care product, typically in the form of a viscous liquid, that is used for cleaning hair or skin coat of animals and possibly removing excess sebum that needs to be diluted with water and washed off.

Leave-in conditioner is a moisturizing conditioner that doesn't need to be rinsed and can have a skin conditioning or cleansing properties Ointments are smooth oily or paraffin/Wax based preparations that is rubbed on the skin for medicinal purposes or as a cosmetic.

A spray is a liquid kept under pressure in a can or other container, which you can force out in very small drops or a liquid or A liquid minutely divided as by a jet of air or steam. Creams are semi-solid emulsions which contain mixtures of oil and water. Their consistency varies between liquids and solids.

Some embodiments provide a canine topical formulation for treating a canine in need thereof. The canine can be a dog, a cat or a horse. In some embodiments, the disclosure provides a canine topical formulation for treating a dog. In some embodiments, the canine topical formulation for treating a dog is shampoo.

In one aspect, in vitro studies showed that Silver ions and 0.1% silver containing Hexazole® (having Cetrimonium chloride—a topical antiseptic and surfactant, Water-diluent/extender; Nonoxynol-12-surfactant and as an emulsifier; Lauramide DEA-Foaming agent/foam booster; PEG-150 Distearate-thickening agent) shampoo are effective in eradicating the biofilms of *S. pseudintermedius* and *Pseudomonas aeruginosa.*

In another aspect, in vitro studies showed that Silver ions and a topical product containing 0.1% silver were effective in eradicating the biofilms of clinical isolates of *S. pseudintermedius* and *Pseudomonas aeruginosa*, including MSRP and MDR *Pseudomonas aeruginosa*. The notable difference is that current studies evaluated the clinical isolates including MSRP and MDR *Pseudomonas aeruginosa*, thus has more direct relevance to clinical scenarios.

Hairs collected from dogs bathed with topical product containing MicroSilver BG® (2% Chlorhexidine and 2% Miconazole with 0.1% MicroSilver BG®) and 0.05% ceramide had a zone of inhibition, against Staphylococcuspseudintermedius, that was larger than the zone of inhibition and was statistically significant, than from dogs bathed with DOUXO® Chlorhexidine Shampoo and MiconaHex®+Triz® Shampoo. The zone of inhibition from dogs bathed with Treatment Product 1 (TP1) was numerically larger than the zone of inhibition from dogs bathed with Malaseb® Shampoo. These results suggest the superior residual antimicrobial activity of TP1 Shampoo.

At day 7, the zone of inhibition of Treatment Product 1 (TP1) Shampoo was:

2.9 times larger than CEVA's DOUXO® Chlorhexidine Shampoo 2.0 times larger than Dechra's MiconaHex®+Triz® Shampoo 1.2 times larger than Bayer's Malaseb® Shampoo as shown in FIG. 1.

The clinical study showed that Treatment product 1 shampoo once a week for 2 weeks is effective against treating Canine SSBP caused by *Staphylococcus pseudintermedius* including MRSP and prevents reinfection because of the residual effective and the biofilm disruption ability of the formulation.

Some embodiments provide a topical formulation of Chlorhexidine 2%, Miconazole 2%, Silver 0.1% and ceramide 0.05% and for the eradication of biofilms of *Staphylococcus* MSRP and MDR *Pseudomonas Aeruginosa.*

Some embodiments provide methods of treating and preventing the reinfection of canine SSBP, shorter treatment duration and frequency and higher treatment compliance.

Some embodiments provide methods of Improving skin conditions of affected dogs due to the residual activity and skin conditioning effect of the formulation.

Some embodiments provide methods of preventing the development resistance by completely eradicating the resistant strain and disrupting the biofilm allowing optimal MICs in contact with the bacterium and preventing clonal selection of pathogenic bacteria to develop resistance.

Disclosure provides methods of preparing a canine topical formulation, wherein the canine topical formulation includes chlorhexidine gluconate, an azole component, a silver component and a ceramide, wherein the method of preparing the canine topical formulation includes:

preparing a mixture having chlorhexidine gluconate, the azole component and a surfactant to form a first mixture;

mixing the ceramide with the first mixture to form a second mixture;

adding a suspension-premix of the silver component into the second mixture to obtain a third mixture;

stirring the third mixture at a temperature below 40 degrees Celsius until a stirred third mixture is obtained, wherein the stirred third mixture is the canine topical formulation, wherein the surfactant is selected from the group consisting of sodium lauryl sulfate and sodium laureth sulfate, wherein the suspension-premix of the silver component is prepared by suspending the silver component in a suspending agent, and wherein the suspending agent is selected from the group consisting of cocamidopropyl betaine, acrylates copolymer, polysorbate 20, ethylene glycol monostearate, triethanolamine and combinations thereof.

It will be readily understood by the skilled artisan that numerous alterations may be made to the examples and instructions given herein. These and other objects and features of present invention will be made apparent from the following examples. The following examples as described are not intended to be construed as limiting the scope of the present invention.

EXAMPLES

Example 1

A mixture having chlorhexidine gluconate, miconazole, and surfactants was prepared. Ceramide III (N-Octadecanoylphytosphingosine) as described below was added after the surfactants were incorporated into the mixture. Silver component was added last as a suspension-premix after addition of ceramide and is described further below. Incorporation of Ceramide III:

Ceramide was added after the addition of surfactants sodium laureth sulphate (SLES) and sodium lauryl sulphate (SLS). It was very important, that the ceramide was clearly and completely dissolved at the beginning of the process. The batch was heated to 90 degrees Celsius. Mixing was continued for at least 2 hours at this temp before the cooling down of the batch.

Preparation of MicroSilver BG®/Syncrystal® Silver Powder Suspension:

A suspension—premix was made by slowly adding the MicroSilver BG® (Bio-Gate AG, Bremen, Germany)

in increments into the suspending agent while stirring the mixture. After it was fully added, the suspension was stirred for 30-45 min using a propeller mixer. The suspension became very dark (almost black). There was no lead time between stirring and adding the suspension-premix to the mixture having chlorhexidine gluconate, miconazole nitrate, surfactants and ceramide.

Incorporation of MicroSilver BG® suspension into the topical product:

MicroSilver BG® was incorporated into the topical product usually at the end of the compounding process.

The suspension was added slowly over some time and when the batch was under temperatures of 40 degrees Celsius. Both batch and premade suspension were stirred during the addition. After the suspension was added, stirring was continued for some time. In most cases, the product was mixed during the cooling process. The length of time depends on the product and mostly on the machinery used.

The canine topical formulation product turned slightly gray depending on the concentration of the premix.

Example 2

I. Introduction:

The anti-biofilm activity of different concentrations of micronized silver and undiluted Treatment Product 1 Shampoo product was tested. Multi-drug resistant clinical isolates of *Pseudomonas aeruginosa* PAE 1103 and Methicillin-resistant *Staphylococcus pseudintermedius* (MRSP) were used as test organisms. The antimicrobial activity of the test articles was compared with standard antibiotics. Ciprofloxacin was used as a positive control against *P. aeruginosa* PAE 1103 and Gentamicin was used as a positive control against Methicillin-resistant *Staphylococcuspseudintermedius* (MRSP). The QC strain of *P. aeruginosa* ATCC 27853 with standard antibiotic (Ciprofloxacin) was used to validate the MBEC assay.

II. Materials and Methods:

II.A. Bacterial Strains:

*P. aeruginosa* ATCC 27853 was obtained from American Type Culture Collection (ATCC) and were maintained as a frozen glycerol stock at −80° C. Multi-drug resistant clinical isolates of *P. aeruginosa* and MRSP were obtained from Microbial Research Inc., Colorado and details of the isolates are provided in table 1.

| Isolate ID | Strain designation | Source of Culture infection | US Region of isolation |
|---|---|---|---|
| *Pseudomonas aeruginosa* - Multi-drug Resistant (MDR) | PSAE-1103 | Human - Blood | Unknown |
| Methicillin resistant *Staphylococcus pseudintermedius*(MRSP) | ISU-8 | Canine Skin | Midwest |

Working bacterial stock was prepared by thawing a glycerol stock, and streaking it onto Tryptic Soy Agar (TSA). Both strains were grown at 37° C. for 24 hours. Inoculum for the study was prepared by suspending isolated colonies in phosphate buffered saline (PBS) and adjusting to approximately $1.5 \times 10^8$ CFU/mL.

*Pseudomonas aeruginosa* was confirmed to be MDR and was verified by the source, Microbial Research, Inc. as shown by having resistance to at least three antibiotic classes. It was actually resistant to at least one antibiotic in all 11 classes that were represented in this panel.

The methicillin-resistant Staphylococcuspseudintermedius (MRSP) was verified by the source, Microbial Research, Inc. as indicated by the oxacillin resistance. These isolates were PBP 2a positive which is the confirmatory test of the mecA gene coding for methicillin-resistance according to CLSI document VET01.

II.B. Minimum Biofilm Eradication Concentration:

Minimum biofilm eradication concentration (MBEC) values provide estimates on the concentration of an antimicrobial product required to kill bacterial biofilm.

II.C. Biofilm formation

The Calgary Biofilm Device (CBD) plate allows for biofilm formation on a lid containing 96 pegs. The inoculum was diluted to $1 \times 10^7$ CFU/mL in Tryptic Soy Broth (TSB) before inoculating the Calgary Biofilm Device (CBD) plate. The CBD plate was incubated with

*P. aeruginosa* (PAE 1103, ATCC 27853) and MRSP for 6 hours at 35° C. on a shaker at 150 rpm. The MBEC assay was conducted as described in Ceri et al.

II.D. Treatment of Biofilm with Test Articles and Standard Antibiotics

Treatment plate was prepared with 0.5%, 0.4%, 0.3%, 0.2%, 0.1%, and 0.05% v/v micronized silver test articles as well as undiluted Treatment Product 1 Shampoo. All test articles were tested in triplicate. The cation-adjusted Mueller Hinton Broth (CA-MHB) was used as negative controls. Ciprofloxacin against *P. aeruginosa* ATCC 27853 was used as QC for MBEC. The CBD plate was first rinsed in PBS and then transferred to the treatment plate. The treated plate was incubated for 24 hours at 35° C. After incubation, the treated CBD plate was rinsed in PBS twice and transferred to a recovery plate containing fresh media. The CBD plate was sonicated in a water bath sonicator for 30 minutes to detach any remaining adherent biofilm. The plate was incubated overnight at 35° C. to evaluate growth. The undiluted TP1 Shampoo left behind residue even after the wash steps, which detached during sonication, making it impossible to determine MBEC with similar methods as other test articles. The presence of biofilm instead was determined by 1:10 serially diluting the corresponding wells from the recovery plate after sonicating in PBS. Dilutions were drop plated on Tryptic Soy Agar (TSA) and incubated for 24 hours at 37° C.

Results:

The lowest concentration of micronized silver test article that inhibited the formation of biofilm of *P. aeruginosa* PAE 1103 and MRSP was determined to be s 0.05% v/v (Table. 2). TP1 Shampoo was only tested at full concentration and eradicated the biofilm of both bacterial strains. Ciprofloxacin had a MBEC value of 0.25 µg/mL against *P. aeruginosa* PAE 1103.

Gentamicin had an MBEC of 0.25 µg/mL against MRSP (Table. 2). The MBEC value for Ciprofloxacin against the QC strain, *P. aeruginosa* ATCC 27853 was 1 µg/mL (Table. 3), and was comparable to our previous work and other published work (Ceri H et al., 1999).

TABLE 2

MBEC values for test articles and
standard antibiotics against test strains

| | MBEC | |
| Treatment | *P. aeruginosa* PAE 1103 | *S. pseudintermedius* (MRSP Clinical isolate) |
|---|---|---|
| Ciprofloxacin | 0.25 μg/mL | NA |
| Gentamicin | NA | 0.25 μg/mL |
| Micronized silver | ≤0.05% | ≤0.05% |
| TP1 Shampoo | Full strength | Full strength |

NA - Not Applicable, Ciprofloxacin was tested only against *P. aeruginosa* and Gentamicin was tested only against *S. pseudintermedius*.

TABLE 3

MBEC values for standard antibiotics
against QC strain, *P. aeruginosa* ATCC 27853.

| Treatment | MBEC *P. aeruginosa* ATCC 27853 |
|---|---|
| Ciprofloxacin | 1 μg/mL |

IV. Discussion & Conclusion:

The full-strength undiluted TP1@ shampoo and micronized silver test article even at the lowest concentration of 0.05% v/v completely eradicated the biofilm of multidrug resistant strains of
   *P. aeruginosa* PAE 1103 and MRSP.

V. References:

1. Ceri H, Olson M E, Stremick C, et al. The Calgary Biofilm Device: New Technology for Rapid Determination of Antibiotic Susceptibilities of Bacterial Biofilms. *Journal of Clinical Microbiology*. 1999; 37(6): 1771-6.

Example 3

Comparative Efficacy study of Residual in vitro activity of canine hair against *Staphylococcus pseudintermedius* and *Malassezia pachydermatis* following a single antimicrobial bath.

The purpose of this investigation was to evaluate 4 antimicrobial shampoos commonly used by practitioners to determine if differences existed between these products regarding residual in vitro activity on canine hair against Methicillin Resistant *Staphylococcus pseudintermedius* and Malasseziapachydermatis following a single application. It was hypothesized (i) no significant in vitro differences between the evaluated shampoos would be observed; (ii) measurable residual activity against both pathogens would be observed through the last time point for all evaluated shampoos by measuring the microbial zone of inhibition by the shampoos. Hairs collected from dogs bathed with Treatment Product 1 Shampoo containing MicroSilver BG® (2% Chlorhexidine and 2% Miconazole with 0.1% MicroSilver BG®) had a zone of inhibition, against *Staphylococcus pseudintermedius*, that was larger than the zone of inhibition and was statistically significant, from dogs bathed with DOUXO® Chlorhexidine Shampoo and MiconaHex®+Triz® Shampoo. The zone of inhibition from dogs bathed with Treatment Product 1 Shampoo was numerically larger than the zone of inhibition from dogs bathed with Malaseb® Shampoo as shown in FIG. 1. These results suggest the superior residual antimicrobial activity of Treatment Product 1 (see Example 4) Shampoo. At day 7, the zone of inhibition of Treatment Product 1 Shampoo was:
   2.9 times larger than CEVA's DOUXO® Chlorhexidine Shampoo;
   2.0 times larger than Dechra's MiconaHex®+Triz® Shampoo;
   1.2 times larger than Bayer's Malaseb® Shampoo.

Example 4

Effectiveness of a formulation of chlorhexidine gluconate, miconazole nitrate, ceramide 3 and silver shampoo Treatment Product 1 Shampoo, chlorhexidine 2%, miconazole 2%, Microsilver BG® 0.1%, ceramide 0.05%) in the treatment of canine secondary superficial bacterial pyoderma compared to a single active ingredient, chlorhexidine gluconate 4% Shampoo: a randomized, blinded, single site, positive-controlled study.

Summary
   1 Study Objective
   2 Study Schedule
   2.1 General Study Design
   2.2 Randomization
   2.3 Treatment product (TP)
   2.4 Control Product (C4)
   2.5 Topical application
   2.6 Prohibited Treatments
   2.7 Permitted Concomitant Treatments
   3 Animals
   3.1 Inclusion Criteria
   3.2 Exclusion Criteria
   3.3 Removal of an animal from the study
   4 Study Site
   4.1 Clinical Study Site
   4.2 Microbiology
   5 Microbiological Culture
   6 Assessment of Effectiveness
   6.1 Primary Criteria: Success or Failure
   6.2 Secondary Criteria: Evolution of SCS over time during Treatment
   7 Data Analysis
   8 Results
   8.1 Population
   8.2 Statistical Methods
   8.2.1 Efficacy evaluation
   8.2.2 Treatment compliance
   8.2.3 Secondary endpoints
   8.3 Study Population
   8.4 Results of Microbiological Culture
   8.5 Clinical Efficacy
   8.5.1 Treatment compliance
   8.5.2 Primary endpoint
   8.5.3 Secondary endpoint: repeated measures of pcs and repeated measures of SCS
   8.5.4 Secondary endpoints:
   8.6 Safety
   8.6.1 Adverse events
   9 Conclusion

Summary

The purpose of this study was to determine if differences exist between TP1 Shampoo, containing 2% Chlorhexidine, 2% Miconazole and 0.1% Silver, and a 4% Chlorhexidine Shampoo (C4) in efficacy when treating canine secondary superficial bacterial pyoderma and the progression/resolution of the respective clinical scores of seborrhea, erythema, lesional spreading and pruritus during the treatment period.

A total of seventy-eight (78) dogs, ages 9.6 weeks to 14.3 years old, weighing from 2.8 to 199 lbs, were enrolled in the study. This included 39, TP1-treated cases and 39.4% Chlorhexidine (C4) treated cases. Nine cases (9) were excluded from the effectiveness evaluation. The reason for exclusion was failure to confirm a viable isolate during bacterial identification and minimum inhibitory concentration testing. *Staphylococcus pseudintermedius* was isolated from 69 dogs, including 14 methicillin-resistant strains (MRSP).

Treatment Product 1 (TP1) Shampoo was applied topically once a week for two weeks (Day 1 and Day 8) and 4% Chlorhexidine shampoo, used as control, was applied twice a week for 2 weeks (Day 1, Day 4, Day 8, and Day 12). Efficacy evaluations were conducted on Day 17 (Visit 3: Initial evaluation of treatment success, 5 days post treatment cessation of C4 application and 9 days post treatment cessation of TP1 application) and on Day 24 for any relapses (Visit 4: Final efficacy evaluation of treatment success).

Based upon a reduction of the Primary Clinical Scores (PCS) to 0 at both the efficacy evaluation points (V3 and V4), the superiority of TP1 treatment over C4 was demonstrated by a statistically significant increase in the percentage of dogs that were successfully treated (88.2% success rate in TP1-treated dogs vs. 40% success rate in C4-treated dogs; p=0.000031). Furthermore, the evolution of all four of the Secondary Clinical Scores (seborrhea, erythema, lesional spreading, and pruritus) throughout the treatment period was superior in the TP1-treated group versus the C4-treated group. As treatment progressed, skin and coat condition improved more in the TP1 group compared to the C4 group; there were no other differences noted between the two treatment groups during the physical examinations conducted during the study.

Thirty-five-point two nine percent (35.29%) of the dogs in the TP1 group had at least one adverse event and 34.3% of the dogs in the C4 group had at least one adverse event, but there was no statistically significant difference between the groups (P=0.931213). None of the dogs throughout the study experienced an adverse event probably linked to treatment.

In conclusion, TP1 Shampoo when applied topically once a week for two weeks was effective and superior in the treatment of secondary superficial bacterial pyoderma in dogs caused by susceptible strains of *Staphylococcus pseudintermedius* and was well tolerated by the study population with no significant adverse events or other deleterious health effects. The product also demonstrated sustained antibacterial effects lasting over weeks as evidenced by absence of relapses after the cessation of TP1 topical therapy.

1 Study Objective

The objective of this clinical study was to determine if differences exist between TP1 Shampoo, containing 2% Chlorhexidine, 2% Miconazole and 0.1% Silver, and a 4% Chlorhexidine Shampoo (C4) in efficacy when treating canine secondary superficial bacterial pyoderma and the progression/resolution of the respective clinical scores of seborrhea, erythema, lesional spreading and pruritus during treatment period.

2 Study Schedule

Study initiation: June 1, 2022
Start of experimental phase: June2, 2022
Study completion date: October 9, 2022

2.1 General Study Design

The study was a two-group, parallel, single-center, well-controlled, blinded, and randomized clinical field study in naturally afflicted dogs. The study assessed if differences exist between TP1 Shampoo, containing 2% Chlorhexidine, 2% Miconazole and 0.1% Silver, and a 4% Chlorhexidine Shampoo (C4) in efficacy when treating canine secondary superficial bacterial pyoderma and progression/resolution of the respective clinical scores of seborrhea, erythema, lesional spreading and pruritus during the progression of the treatment.

Key elements of the study:
78 dogs were enrolled (39-TP1 cases and 39-C4 cases).
One study site contributed cases to the analysis.
General (non-specialist) veterinary practitioners served as Investigators.
Subjects were evaluated for secondary superficial bacterial pyoderma, and those meeting enrollment criteria were randomized to one of two treatment groups.
Both the Investigator and pet owner were blinded to treatment (neither was aware of a dog's treatment group).
Effectiveness of were determined by measuring the improvement of three types of primary clinical signs [(PCS), papules, pustules, and/or folliculitis], 5 days post treatment cessation of C4 application and 9 days post treatment cessation of TP1 application, (V3-initial evaluation of treatment success) and one week later (V4-final evaluation of treatment success). Treatment was considered successful if all primary clinical signs were absent at both the evaluations.
Seborrhea, erythema, pruritus, and lesional spreading were assessed as secondary endpoints.
Physical examinations were conducted on all visits and assessed the skin/haircoat conditions.
Table 1 lists the application days for both TP1 and C4

TABLE 1

| Application days of treatment | |
| --- | --- |
| Treatment article | Treatment Days |
| TP1 | Day 1 and Day 8 |
| C4 | Day 1, Day 4, Day 8, and Day 12 |

Initial treatment success was measured on Day 17 (V3). All dogs considered to be preliminary treatment successes were evaluated again for final treatment success on Day 24 (Visit 4). For a case to be declared as a treatment success, all primary clinical signs (papules, pustules, and/or folliculitis) must have remained absent at both Visit 3 and Visit 4. All dogs with PCS on Visit 3 were declared as treatment failures. All relapsed cases at Visit 4 were also declared as treatment failures.

2.2 Randomization

Randomization of treatment groups was achieved by a random number table. At the inclusion visit (Day 1), if inclusion criteria were met, dogs were assigned to one of the two treatment groups by a technician (nonblinded person) by the chronological order the dog was enrolled in the study: group T (TP1) and group C(C4).

A unique five-character case ID was assigned to each case using the first three letters of the last name of the Investigator and a two-digit number corresponding to the chronological order that the case was assigned to the study within a given study site (e.g., the second case for Dr. Jones would have been identified as JONO2). Dogs were randomized to TP1 or C4 groups in a ratio of 1:1.

A positive bacterial culture result supporting the diagnosis of canine secondary superficial bacterial pyoderma was a requirement for inclusion in the efficacy population. However, before culture results were received, all dogs meeting the inclusion and exclusion criteria specified in the protocol were randomized at Visit 1 and assigned to one of the two treatment groups in the chronological order as described above. Subsequently, dogs with negative culture results were withdrawn from the study at Visit 2. The dispensing technician dispensed the test article as per the Study Animal Log. The study evaluated the effectiveness in a field setting; thus, no attempt was made to equalize for gender, age, or body weight. The clinical evaluator was blinded to the identity of the treatment group.

2.3 Treatment Product (TP1)

The TP1 (was a formulation of chlorhexidine gluconate, miconazole nitrate, ceramide 3 and elemental silver shampoo (chlorhexidine 2%, miconazole 2%). TP1 was packaged and supplied to the study site in white HDPE bottles. Batches used in the study, identified as Lot #s 22104 and 22105.

2.4 Control Product (C4)

The control product was a single active ingredient, chlorhexidine gluconate 4% Shampoo and was packaged and supplied to the study site in white HDPE bottles. The batches used in the study were identified by lot numbers 1L05 and 1L06.

2.5 Topical Application

TP1 and C4 Shampoo was applied as per the label instructions ("Shake well before use. Wet the hair coat with warm water and apply small quantities of the shampoo from the base of the neck to the base of the tail. Massage shampoo over pet's body to ensure good contact with the skin. Allow to remain on hair for 5 to 10 minutes, then rinse thoroughly with clean water and repeat").

TP1 was applied once a week for two weeks. C4 was applied twice a week for 2 two weeks. Study articles (TP1 or C4) were dispensed, in quantities sufficient to permit topical application for 9 days, based on the animal's body size at that visit. Pet owners were instructed to apply the products.

2.6 Prohibited Treatments

The following treatments were prohibited during the study because their use would have confounded interpretation of the results.

topical dermatological treatments: medicated shampoos and sprays, soothing shampoos, and lotions (i.e., oatmeal or chamomile products), medicated flea shampoos, and medicated ointments or lotions (other than the test articles),
  antibiotics,
  non-steroidal anti-inflammatory drugs (NSAIDs),
  corticosteroids,
  immunomodulators.

2.7 Permitted Concomitant Treatments

All treatments of any permitted medication administered concomitantly with the test article were documented on the Concomitant Medication Form by the Investigator. Permitted concomitant treatments included:

treatments or preventatives for fleas except as noted above.
  treatment of the dog's environment for ectoparasites in accordance with manufacturer recommendations.
  anthelmintics, and vaccines; and/or
  treatments for stable concomitant diseases.

3 Animals

The target study population consisted of dogs that were:
  12 weeks or older, of any breed
  male or female, neutered or intact
  non-pregnant and non-lactating, and
  client-owned (not pound- or shelter-owned).

3.1 Inclusion Criteria

Dogs enrolled in the study had clinical lesions of secondary superficial bacterial pyoderma characterized by a mild, moderate or severe scoring of one or more of the following Primary Clinical Signs (PCS), at the time of enrollment: papules, pustules, and/or folliculitis. Scoring of the PCS was done on a 0 to 3 scale:

0=(Absent) No clinical signs characteristic of canine secondary superficial bacterial pyoderma present
  1=(Mild) 1 to 4 lesions per 100 $cm^2$
  2=(Moderate) 5 to 15 lesions per 100 $cm^2$
  3=(Severe) More than 15 lesions per 100 $cm^2$ Lesions were measured where the lesions appeared to be the most numerous. The presumptive diagnosis of a clinically apparent canine secondary superficial bacterial pyoderma was confirmed by a positive culture obtained at the time of enrollment. As indicated in section 3.3, dogs with negative bacterial culture results were withdrawn from the study at Visit 2.

3.2 Exclusion Criteria

Dogs not having a positive pre-treatment bacterial culture and dogs not scoring at least one mild, moderate, or severe rating in one of the PCS were excluded from the study.

3.3 Removal of an Animal from the Study

Per protocol, animals were removed from the study during follow-up visits if: they developed concomitant diseases that interfered with the evaluation of the response to treatment, they received prohibited treatment/s (see Section 2.6)
  they experienced an adverse event(s) that required stopping the treatment with test article (TP1 or C4) and/or starting treatment with a prohibited drug
  cultured lesions did not confirm a bacterial infection,
  the owners withdrew consent, or the owners failed to comply with the protocol.
  If an animal was removed from the study, the Investigator notified the Study Sponsor. Removal was documented on the Early Withdrawal Form.

4 Study Site 4.1 Clinical Study Site

The study was conducted at HEALTHY PETS VETERINARY HOSPITAL, Indira Nagar, Karnataka, India. The Sponsor ensured that Investigators and site personnel were qualified by experience and training.

4.2 Microbiology

Microbiological activities of the study, including culture, identification, and Minimum Inhibitory Concentrations (MIC) determination, were conducted by the contract service of the Clinical Research Incorporated (CRI). CRI is a private microbiological service. Contact information for CRI is: 14 Service Road, Sanjayanagara, Bengaluru, Karnataka 560024, India 5 Microbiological Culture

*Staphylococcus pseudintermedius* because of its common association with pyoderma, was identified apriori for speciation and enumeration.

At Visit 1 (Day 1), a sample was collected for microbiological culture to identify the pathogen(s) responsible for the infection. Also, at any time a dog exited the study, samples were taken for microbiological culture, if there were any lesions to culture. Additionally, a sample was collected for microbiological evaluation at the initial and final evaluation days (V3 and V4), if there were any lesions to culture.

Samples were collected from pustules by first cleaning the area around the pustule to be sampled, then opening the pustule with a sterile hypodermic needle and collecting the contents of the pustule onto a sterile swab.

Samples were identified using the Lab Sample Form provided with the Case Report Forms (CRFs) which contained the following information:

study number,
Investigator name,
name of dog (in case ID was not readable),
case identification number,
date of sampling, and
visit number.

The samples were packed into a cooler with cold packs for transport and sent to the laboratory along with their Lab Sample Form via overnight delivery.

Once the laboratory received the culturette, the culture media was inoculated to isolate and identify the bacteria causing the infection.

6 Assessment of Effectiveness

The success or failure of topical therapy was based solely on the PCS and microbiological outcomes. The outcome of the secondary signs was used to further characterize treatment progression while under therapy but was not used to judge success or failure of TP1 or C4 topical therapy.

6.1 Primary Criteria: Success or Failure

Cases were evaluated individually for their response to treatment. A case was considered a treatment success if there were no lesions to culture on Day 17, (Visit 3) and one week later (Day 24, Visit 4). An animal was considered a treatment failure if the animal exited the study due to a lack of clinical progress, or if the clinical signs (lesions) of pyoderma were still present on Visit 3 or on Visit 4.

6.2 Secondary Criteria: Evolution of SCS over time during Treatment

The Investigator and owner also assessed four secondary clinical signs at each visit:

seborrhea,
erythema,
lesional spreading (except the first visit),
and pruritus (Owner evaluation)

The evolution of the secondary clinical scores (SCS) over time during the treatment period was used to further characterize treatment effectiveness.

Scoring of the SCS was done on a 0 to 3 scale:

0=(Absent) No clinical signs present
1=Mild
2=Moderate
3=Severe

Skin and coat conditions were assessed from V1 to V3 and were given a score of 1 to 3:

1=Poor
2=Satisfactory
3=Good

Data Analysis

Except for microbiological data, all data were collected by the Investigator or other authorized study site personnel according to the study protocol and amendments and recorded on study-specific paper Case Report Forms (CRFs). Corrections to the CRFs were made by the Investigator or other authorized study personnel. The Investigator dated and verified all corrective entries with initials.

Following completion of data entry and resolution of all queries, the protocol-compliant population was determined during a blind review of data. After the population determination, the database was locked, and the locked database was used for the final statistical analysis for study reporting.

8 Results

8.1 Population

The dog was the experimental unit. The population for efficacy analysis consisted of all dogs for which all admission criteria were met, and no exclusion criterion were identified. Details on the efficacy population are provided in section 8.3

8.2 Statistical Methods 8.2.1. Efficacy Evaluation

The primary outcome variable was treatment success (yes or no), as defined in Section [0289]. The percent success and 95% confidence intervals were used as summary statistics.

8.2.2 Treatment Compliance

Dosing compliance was described by treatment group with mean, standard deviation, median, minimum, and maximum, and was compared between treatment groups with Wilcoxon test. This analysis was performed on the efficacy population.

8.2.3. Secondary Endpoints

Evolution of PCS and SCS over time during treatment was assessed and reported as means of the scores.

8.3 Study Population

A total of seventy-eight (78) dogs, ages 9.6 weeks to 14.3 years old, weighing from 2.8 to 199 lbs, were enrolled in the study and received at least one application of either the TP1 or C4. Table 2 lists the dogs enrolled in the study, their treatment allocation (TP1 or C4), whether they were included in either the efficacy population, or the reason for non-inclusion in the efficacy population.

TABLE 2

Enrolled cases and reason(s), if any, for non-inclusion in efficacy population

| # | Case ID | Trt* | Pop** | Reason for non-inclusion in the efficacy population |
|---|---------|------|-------|-----------------------------------------------------|
| 1 | BAK01 | TP1 | E | |
| 2 | BAK02 | C4 | E | |
| 3 | BAK03 | TP1 | E | |
| 4 | BAK04 | C4 | N/A | Negative Culture |
| 5 | BAK05 | TP1 | E | |
| 6 | BAK06 | C4 | E | |
| 7 | BAK07 | TP1 | E | |
| 8 | BAK08 | C4 | N/A | Negative Culture |
| 9 | BAK09 | TP1 | E | |
| 10 | BAK10 | C4 | E | |
| 11 | BAK11 | TP1 | N/A | Negative Culture |
| 12 | BAK12 | C4 | E | |
| 13 | BAK13 | TP1 | N/A | Negative culture |
| 14 | BAK14 | C4 | E | |
| 15 | BAK15 | TP1 | E | |
| 16 | BAK16 | C4 | E | |
| 17 | BAK17 | TP1 | N/A | Negative Culture |
| 18 | BAK18 | C4 | E | |
| 19 | BOM01 | TP1 | N/A | Negative Culture |
| 20 | BOM02 | C4 | E | |
| 21 | BOM03 | TP1 | E | |
| 22 | BOM04 | C4 | E | |
| 23 | BRY01 | TP1 | N/A | Negative culture |

TABLE 2-continued

| | | | | Enrolled cases and reason(s), if any, for non-inclusion in efficacy population |
|---|---|---|---|---|
| # | Case ID | Trt* | Pop** | Reason for non-inclusion in the efficacy population |
| 24 | BRY02 | C4 | E | |
| 25 | BRY03 | TP1 | E | |
| 26 | BRY04 | C4 | E | |
| 27 | BRY05 | TP1 | E | |
| 28 | BRY06 | C4 | E | |
| 29 | BRY07 | TP1 | E | |
| 30 | BRY08 | C4 | E | |
| 31 | CAM01 | TP1 | E | |
| 32 | CAM02 | C4 | E | |
| 33 | CAM03 | TP1 | E | |
| 34 | CAM04 | C4 | E | |
| 35 | CAM05 | TP1 | E | |
| 36 | CAM06 | C4 | E | |
| 37 | CAM07 | TP1 | E | |
| 38 | CAM08 | C4 | E | |
| 39 | CAM09 | TP1 | E | |
| 40 | CAM10 | C4 | E | |
| 41 | CAM11 | TP1 | E | |
| 42 | CAM12 | C4 | N/A | Negative Culture |
| 43 | CAM13 | TP1 | E | |
| 44 | CAM14 | C4 | E | |
| 45 | CAM15 | TP1 | E | |
| 46 | CIN01 | C4 | E | |
| 47 | CIN02 | TP1 | E | |
| 48 | CIN03 | C4 | E | |
| 49 | CIN04 | TP1 | E | |
| 50 | CIN05 | C4 | E | |
| 51 | CIN06 | TP1 | E | |
| 52 | CIN07 | C4 | E | |
| 53 | CIN08 | TP1 | E | |
| 54 | CIN09 | C4 | E | |
| 55 | CIN10 | TP1 | E | |
| 56 | CIN11 | C4 | E | |
| 57 | CIN12 | TP1 | E | |
| 58 | CIN13 | C4 | E | |
| 59 | CLE01 | TP1 | E | |
| 60 | CLE02 | C4 | E | |
| 61 | CLE03 | TP1 | E | |
| 62 | CLE04 | C4 | | |
| 63 | CLE05 | TP1 | E | |
| 64 | CLE06 | C4 | E | |
| 65 | CLE07 | TP1 | E | |
| 66 | GEL01 | C4 | E | |
| 67 | GEL02 | TP1 | E | |
| 68 | GEL03 | C4 | E | |
| 69 | GEL04 | TP1 | E | |
| 70 | GEL05 | C4 | E | |
| 71 | GEL06 | TP1 | E | |
| 72 | GEL07 | C4 | E | |
| 73 | GEL08 | TP1 | E | |
| 74 | GEL09 | C4 | N/A | Negative Culture |
| 75 | GEL10 | TP1 | E | |
| 76 | GEL11 | C4 | E | |
| 77 | GEL12 | TP1 | E | |
| 78 | GEL13 | C4 | E | |

*Trt. = Treatment group: TP1, C4.
**Pop. = population: E: Efficacy population; N/A: Not applicable Of the 78 cases enrolled, randomized, and topically dosed, nine (9) cased were excluded from the effectiveness evaluation (5 from the TP1 group and 4 from the C4 group).

8.4 Results of Microbiological Culture

Staphylococcuspseudintermedius was isolated from 69 dogs, including 14 methicillin-resistant strains (MRSP). The MICs values ranged from 0.5 µg/ml to 4 µg/ml for both. The $MIC_{90}$ of MRSP was 2 µg/ml and MSSP $MIC_{90}$ was 1 µg/ml 8.5 Clinical Efficacy 8.5.2 Treatment Compliance Treatment (dosing application) compliance was 100% for both groups and thus no statistical analysis was performed.

8.5.2 Primary Endpoint

The percentage of successful treatment in the efficacy population (as defined on section 2.1) is listed in Table 3. After 2 weeks of treatment, PCS were absent in 88.2% of the dogs, on both V3 (Day 17) and V4 (Day 24) in the TP1 group, whereas PCS were absent in 57.14 of the dogs on V3 and 40% of the dogs on V4 (at the final evaluation treatment success); this difference was statistically significant (p=0.000031).

TABLE 3

| | Primary endpoint: Percentage of Successful Treatment (Efficacy Population) | | |
|---|---|---|---|
| Treatment | TP1 | C4 | p-value |
| N | 34 | 35 | |
| Failures | 4 | 21 | |
| Success | 30 (88.2%) | 14 (40%) | 0.000031 |

Number of dogs with PCS absent (PCS score of 0) and PCS present on Visit 3 and Visit 4 are listed in Table 4.

TABLE 4

| | Number of dogs with PCS absent (PCS score of 0) and PCS present on Visit 3 and 4 | | | |
|---|---|---|---|---|
| | V3 (initial evaluation of treatment success) | | V4 (final evaluation of treatment success) | |
| | TP1 Group (n = 34) | C4 Group (n = 35) | TP1 Group (n = 34) | C4 Group (n = 35) |
| PCS 0 (absent) | 30 | 20 | 30 | 14 |
| PCS present | 4 | 15 | 4 | 21 |

On Visit 4 (on the day of final evaluation) six (6), 30%, of the dogs in the C4 group that were declared as initial treatment success (PCS absent), had relapses characterized by the presence of PCS. These dogs were also declared as failures as (as defined on section 2.1).

Secondary endpoint: repeated measures of pcs and repeated measures of SCS Repeated measures of PCS over the treatment period are summarized in Table 5.

TABLE 5

| | Repeated measures of PCS over the treatment period | | | | | |
|---|---|---|---|---|---|---|
| | Repeated measures of PCS | | | | | |
| | Visit 1 | | Visit 2 | | Visit 3 | |
| | TP1 | C4 | TP1 | C4 | TP1 | C4 |
| Papules (Mean) | 1.53 | 1.52 | 0.92 | 1.67 | 0.11 | 0.97 |
| Pustules (Mean) | 1.64 | 1.64 | 1.26 | 1.56 | 0.29 | 0.97 |
| Folliculitis (Mean) | 1.03 | 1.82 | 1.03 | 0.94 | 0.17 | 0.94 |

With respect to Repeated measures of PCS over the treatment period, all the repeated measures analysis showed a significant interaction between time and TP1 treatment group and C4 group.

8.5.4 Secondary Endpoints:

Repeated measures of SCS over the treatment period are summarized in Table 6.

TABLE 6

| Repeated measures of SCS over the treatment period | | | | | |
|---|---|---|---|---|---|
| | Repeated measures of SCS | | | | |
| | Visit 1 | | Visit 2 | | Visit 3 | |
| | TP1 | C4 | TP1 | C4 | TP1 | C4 |
| Seborrhea (Mean) | 1.94 | 2 | 1.03 | 1.91 | 0.17 | 1.14 |
| Erythema (Mean) | 1.9 | 1.85 | 1.4 | 1.58 | 0.5 | 0.94 |
| Lesional spreading (Mean) | | | 0.9 | 1.61 | 0.4 | 0.97 |
| Pruritus (Mean) | 2.6 | 2.2 | 1.3 | 1.59 | 0.5 | 0.98 |

All the repeated measures analysis showed a significant interaction between time and TP1 treatment group and C4 group.

79.41% of the dogs in the TP1 group showed improvement in skin and hair coat conditions compared to 48.51% of the dogs from the C4 group (V1 to V3).

8.6 Safety 8.6.1 Adverse Events

Thirty-five-point two nine percent (35.29%) of the dogs in the TP1 group had at least one adverse event and 34.3% of the dogs in the C4 group had at least one adverse event, but there was no statistically significant difference between the groups (P=0.931213). None of the dogs throughout the study experienced an adverse event probably linked to treatment.

9 Conclusion

In conclusion, TP1 Shampoo when applied topically once a week for two weeks was effective and superior in the treatment of secondary superficial bacterial pyoderma in dogs caused by susceptible strains of *Staphylococcus pseudintermedius*, including MSRP and was well tolerated by the study population with no significant adverse events or other deleterious health effects. The product also demonstrated sustained antibacterial effects lasting over weeks.

Control Study: Efficacy Study of TP2 Shampoo (2% Chlorhexidine and 2% Miconazole with 0.01% MicroSilver BG®) when Applied Topically (Dermal Application) in client owned dogs with naturally afflicted skin infection.

General Design: Open-ended non-placebo controlled study

Test Animals: A total of 8 client owned dogs of different breeds were used in this study. Eight dogs (3 males and 5 females) were treated with TP2 Shampoo.

Dosage form: Final market formulation of TP2 Shampoo containing 2% Chlorhexidine and 2% Miconazole with 0.010% MicroSilver BG® was used. Application sites were observed 15 minutes, 4 and 24 hours post dosing.

Route of application: Dermal (topically)

Dosages used: Treatment group is shown in Table 1.

TABLE 1

| Dose Group | | | | |
|---|---|---|---|---|
| Group | Treatment | Dosage Used | Regimen | No. Dogs |
| T1 | TP2 Shampoo | 30 mL/twice a week for 6 weeks | 30 mL/day applied once daily for 42 days | 3 males and 5 females |

Test duration: forty two days

Clinical parameters evaluated: Veterinary clinical observations, general daily observations, temperature, application site assessments, hematology, serum chemistry, blood sliver and body weight.

Statistical Analysis: Descriptive statistical analysis was performed on the raw data Results:

Clinical observations: There were no treatment-related clinical effects on body weight, behavior, or temperature.

Dosing site observations: There was no dosing site abnormities observed in any of the treated animals (Papules or erythema) during the treatment period.

Clinical Chemistry: There were no treatment-related abnormal clinical chemistry values.

Hematology: There were no treatment-related abnormal hematology values.

Blood silver analysis: Bioanalysis of blood for sliver confirmed that none of the blood samples analyzed were positive for silver [limit of detection for silver was 20 ppb, samples were analyzed at Still Meadow, Inc. using Inductive Coupled Mass Spectrophotometry (ICP/MS)].

Conclusions: Dermal application of TP2 Shampoo to client owned animals with naturally afflicted skin infections at the dose of 30 mL/twice a week for 42 days was well tolerated in all the study animals. TP2 Shampoo was also effective for the treatment of skin conditions in dogs. The effectiveness was determined by veterinary clinical examinations conducted prior to the application of the shampoos, days 7, 14, 21, 28, 35 and after the completion of the treatment, i.e., on day 42. Complete resolution of clinical signs observed only after 6 weeks of therapy.

Other modifications and variations to the invention will be apparent to those skilled in the art from the foregoing disclosure and teachings. Thus, while only certain embodiments of the invention have been specifically described herein, it will be apparent that numerous modifications may be made thereto without departing from the spirit and scope of the invention.

What is claimed is:

1. A canine topical formulation for treating canine secondary superficial bacterial pyoderma, the canine topical formulation comprising:

chlorhexidine gluconate of about 2% by weight, a silver component ranging from about 0.08% to about 0.12% by weight, an azole component ranging from about 0.25% to about 2.2% by weight, and a ceramide ranging from about 0.02% to about 0.05% by weight, wherein the azole component is an azole or a salt of an azole, wherein the canine topical formulation is selected from a group consisting of a shampoo, a conditioner, a leave-on product, a spray, and combinations thereof, wherein the ceramide is completely dissolved in a first mixture comprising chlorhexidine gluconate, the azole component and a surfactant, wherein the surfactant is selected from the group consisting of sodium lauryl sulfate and sodium laureth sulfate, and wherein the canine secondary superficial bacterial pyoderma is caused by *Staphylococcous pseudintermedius*.

2. The canine topical formulation of claim 1, wherein the silver component is selected from the group consisting of elemental silver, micronized silver, nanosilver, a colloidal silver, a silver salt, and combinations thereof.

3. The canine topical formulation of claim 2, wherein the silver salt is selected from the group consisting of silver nitrate, silver chloride, silver sulfadiazine, and combinations thereof.

4. The canine topical formulation of claim 1, wherein the silver component is about 0.1% by weight of the canine topical formulation.

5. The canine topical formulation of claim 1, wherein the silver component is elemental silver.

6. The canine topical formulation of claim 5, wherein the elemental silver is about 0.1% by weight of the formulation.

7. The canine topical formulation of claim 1, wherein the azole is selected from the group consisting of ketoconazole, miconazole, fluconazole, itraconazole, econazole, climbazole and combinations thereof.

8. The canine topical formulation of claim 1, wherein the salt of the azole is selected from the group consisting of a chloride, a nitrate, an amine, and combinations thereof.

9. The canine topical formulation of claim 1, wherein the salt of the azole is miconazole nitrate.

10. The canine topical formulation of claim 9, wherein the miconazole nitrate ranges from about 1.8% to about 2.2% by weight of the canine topical formulation.

11. The canine topical formulation of claim 10, wherein the miconazole nitrate is about 2% by weight of the canine topical formulation.

12. The canine topical formulation of claim 9, wherein the chlorhexidine gluconate is about 2% by weight of the canine topical formulation;

wherein the silver component is about 0.1% by weight of the canine topical formulation; and wherein the miconazole nitrate is about 2% by weight of the canine topical formulation.

13. The canine topical formulation of claim 1, wherein the ceramide is selected from the group consisting of ceramide 1 (ceramide EOP), ceramide 2 (ceramide NS), ceramide 6-II (ceramide AP), ceramide 9 (ceramide EOP), phytosphingosine, sphingosine, ceramide 3 (N-Octadecanoylphytosphingosine), and combinations thereof.

14. The canine topical formulation of claim 13, wherein the ceramide is ceramide 3 (N-Octadecanoylphytosphingosine).

15. The canine topical formulation of claim 13, wherein the ceramide 3 (N-Octadecanoylphytosphingosine) ranges from about 0.025% to about 0.05% by weight of the canine topical formulation.

16. The canine topical formulation of claim 15, wherein the ceramide 3 (N-Octadecanoylphytosphingosine) is about 0.05% by weight of the canine topical formulation.

17. The canine topical formulation of claim 1, wherein the chlorhexidine gluconate is about 2% by weight of the canine topical formulation;

the azole component is miconazole nitrate, wherein the miconazole nitrate is 2% by weight of the canine topical formulation;

the silver component is elemental silver, wherein the elemental silver is about 0.1% by weight of the canine topical formulation; and the ceramide is ceramide 3 3 (N-Octadecanoylphytosphingosine), and wherein the ceramide 3 (N-Octadecanoylphytosphingosine) is about 0.05% by weight of the canine topical formulation.

18. The canine topical formulation of claim 1, further comprising ethylene diamine tetra acetic acid (EDTA).

19. The canine topical formulation of claim 1, further comprising: a component selected from the group consisting of a solvent, an extender, an emulsifier, a suspending agent, a foam booster, a fragrance, and combinations thereof.

20. The canine topical formulation of claim 1, further comprising: purified water, sodium laureth sulfate, sodium lauryl sulfate, cocamidopropyl betaine, acrylates copolymer, Polysorbate 20, ethylene glycol monostearate, triethanolamine, kiwi fragrance, titanium dioxide, synthetic fluorphlogopite, methylchloroisothiazolinone and methylisothiazolinone.

21. The canine topical formulation of claim 1, wherein the canine topical formulation is a shampoo.

22. The canine topical formulation of claim 1 for treating a canine in need thereof, wherein the canine is a dog.

23. The canine topical formulation of claim 1, wherein the canine topical formulation is prepared by a method comprising:

preparing a mixture comprising the chlorhexidine gluconate, the azole component and the surfactant to form a first mixture;

dissolving the ceramide completely in the first mixture to form a second mixture;

adding a suspension-premix of the silver component into the second mixture to obtain a third mixture;

stirring the third mixture at a temperature below 40 degrees Celsius until a stirred third mixture is obtained, wherein the stirred third mixture is the canine topical formulation, wherein the surfactant is selected from the group consisting of sodium lauryl sulfate and sodium laureth sulfate, wherein the suspension-premix of the silver component is prepared by suspending the silver component in a suspending agent, and wherein the suspending agent is selected from the group consisting of cocamidopropyl betaine, acrylates copolymer, polysorbate 20, ethylene glycol monostearate, triethanolamine and combinations thereof.

24. A method of decreasing a biofilm of *S. pseudintermedius*, the method comprising treating a canine in need thereof with the canine topical formulation of claim 1.

25. A method of decreasing a biofilm of *Pseudomonas aeruginosa* comprising treating a canine in need thereof with the canine topical formulation of claim 1.

26. A method of decreasing a biofilm of methicillin resistant *S. pseudintermedius* comprising treating a canine in need thereof with the canine topical formulation of claim 1.

27. A method of decreasing a biofilm of multidrug resistant *Pseudomonas aeruginosa* comprising treating a canine in need thereof with the canine topical formulation of claim 1.

28. A method of improving a skin condition of a dog affected with secondary superficial bacterial pyoderma due to the residual activity of pathogens, the method comprising treating a dog in need thereof with the canine topical formulation of claim 1.

29. The method of claim 28, wherein the skin condition is selected from the group consisting of seborrhea, erythema, lesional spreading (except the first visit), and pruritus.

30. A method of improving skin conditioning in a canine having canine secondary superficial bacterial pyoderma comprising treating a canine in need thereof with the canine topical formulation of claim 1.

31. A method of treating canine secondary superficial bacterial pyoderma wherein the canine topical formulation of claim 1 is applied topically once a week for two weeks to a canine in need thereof.

32. A method of preparing the canine topical formulation of claim 1, the method comprising:

preparing a mixture comprising the chlorhexidine gluconate, the azole component and the surfactant to form a first mixture;

dissolving the ceramide completely in the first mixture to form a second mixture;

adding a suspension-premix of the silver component into the second mixture to obtain a third mixture;

stirring the third mixture at a temperature below 40 degrees Celsius until a stirred third mixture is obtained, wherein the stirred third mixture is the canine topical formulation, wherein the surfactant is selected from the group consisting of sodium lauryl sulfate and sodium laureth sulfate, wherein the suspension-premix of the silver component is prepared by suspending the silver component in a suspending agent, and wherein the suspending agent is selected from the group consisting of cocamidopropyl betaine, acrylates copolymer, polysorbate 20, ethylene glycol monostearate, triethanolamine and combinations thereof.

*    *    *    *    *